United States Patent
Lin et al.

(10) Patent No.: US 7,475,608 B2
(45) Date of Patent: *Jan. 13, 2009

(54) LIQUID MEASURING DEVICE

(75) Inventors: Szu-Min Lin, Laguna Hills, CA (US); Peter Zhu, Irvine, CA (US)

(73) Assignee: Ethicon, Inc., Somerville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/394,049

(22) Filed: Mar. 30, 2006

(65) Prior Publication Data

US 2006/0243044 A1    Nov. 2, 2006

Related U.S. Application Data (63) Continuation of application No. 10/448,554, filed on May 30, 2003, now Pat. No. 7,073,401, which is a continuation of application No. 10/042,906, filed on Jan. 9, 2002, now Pat. No. 6,629,468, and a continuation of application No. 10/042,904, filed on Jan. 9, 2002, and a continuation of application No. 09/810,875, filed on Mar. 16, 2001, now Pat. No. 6,360,595.

(51) Int. Cl.
*G01N 1/00* (2006.01)

(52) U.S. Cl. .................................. 73/863.21

(58) Field of Classification Search ............. 73/863.21, 73/863.23, 64.58, 864.13, 864.16, 864.35; 422/68.1, 82.05, 100, 101; 436/810; 435/30
See application file for complete search history.

(56) References Cited

U.S. PATENT DOCUMENTS

| | | | |
|---|---|---|---|
| 3,921,460 A | 11/1975 | Schmidlin | |
| 3,985,032 A | 10/1976 | Avakian | |
| 4,059,020 A | 11/1977 | Avakian | |
| 4,267,729 A | 5/1981 | Eddelman et al. | |
| 4,327,745 A | 5/1982 | Ford, Jr. | |
| 4,601,212 A | 7/1986 | Shapiro | |
| 4,750,373 A | 6/1988 | Shapiro | |
| 4,794,806 A | 1/1989 | Nicoli et al. | |
| 4,871,662 A | 10/1989 | Rosov | |
| 4,889,692 A | 12/1989 | Holtzman | |
| 4,926,701 A | 5/1990 | Tompkins | |
| 4,936,315 A | 6/1990 | Lineback | |
| 4,961,351 A | 10/1990 | Gerken | |
| 4,973,450 A | 11/1990 | Schluter | |
| 4,999,164 A | 3/1991 | Puchinger et al. | |
| 5,082,150 A * | 1/1992 | Steiner et al. | 222/189.09 |
| 5,104,533 A * | 4/1992 | Szabados | 210/257.1 |
| 5,171,537 A | 12/1992 | Wainwright et al. | |

(Continued)

FOREIGN PATENT DOCUMENTS

EP    241611 A1    10/1987

(Continued)

OTHER PUBLICATIONS

Eiropean Search Report dated Dec. 19, 2003.

*Primary Examiner*—Robert R Raevis (57) ABSTRACT

A liquid measuring device is described for carrying out the assay using a gas or vapor permeable but liquid impermeable membrane barrier to control the volume of liquid to be measured or transferred. The membrane may be used in any instance where a fixed volume of liquid needs to be measured.

11 Claims, 6 Drawing Sheets

U.S. PATENT DOCUMENTS

| | | |
|---|---|---|
| 5,478,526 A | 12/1995 | Sakai et al. |
| 5,496,523 A | 3/1996 | Gazit et al. |
| 5,603,900 A | 2/1997 | Clark et al. |
| 5,783,063 A | 7/1998 | Charkson et al. |
| 5,916,524 A | 6/1999 | Tisone |
| 6,010,269 A * | 1/2000 | Yokosuka et al. ........... 401/217 |
| 6,045,757 A | 4/2000 | Moriarty et al. |
| 6,117,394 A | 9/2000 | Smith |
| 6,360,595 B1 | 3/2002 | Lin et al. |
| 6,368,872 B1 | 4/2002 | Juranas |
| 6,629,468 B2 | 10/2003 | Lin et al. |
| 2002/0192114 A1 | 12/2002 | Lin et al. |
| 2003/0209082 A1 | 11/2003 | Lin et al. |

FOREIGN PATENT DOCUMENTS

| | | |
|---|---|---|
| WO | WO 2000025924 A1 | 5/2000 |

* cited by examiner

Figure 1

Reaction 1

Aldehyde + X ⟶ Compound with first color (Preferably, this is colorless)

Reaction 2 (Preferably, reaction 2 is slower than reaction 1)

Aldehyde + Y ⟶ Compound with second color

LIQUID MEASURING DEVICE

RELATED APPLICATIONS

This application is a continuation of U.S. Ser. No. 10/448,554, filed May 30, 2003 now U.S. Pat. No. 7,073,401 which is a continuation of U.S. Ser. No. 10/042,906, filed Jan. 9, 2002, now U.S. Pat. No. 6,629,468 and a continuation of U.S. Ser. No. 10/042,904, filed Jan. 9, 2002 which are both continuation of U.S. Ser. No. 09/810,875, filed Mar. 16, 2001, now U.S. Pat. No. 6,360,595, issued Mar. 26, 2002.

BACKGROUND OF THE INVENTION

1. Field of the Invention

The field of the invention relates to an apparatus and a method for using the apparatus for the measurement and/or transfer of a fixed volume of liquid sample.

2. Description of the Related Art

General methods to determine o-phthalaldehyde (OPA) or glutaraldehyde concentrations are mainly instrumental measurements that could be classified into chromatographic measurement (chromatographic, HPLC analysis) or non-chromatographic measurement (direct spectroscopic assay). For HPLC analysis, OPA or glutaraldehyde are measured by both a derivative method or a non-derivative method. The most common derivative method is to convert OPA or glutaraldehyde to 2,4-dinotrophenylhydrazones by reacting OPA with 2,4-dinitrophenylhydrazine. Since the UV absorption is greatly enhanced, this method is valuable for low level OPA or glutaraldehyde measurements especially in environmental analysis. For measurements of high concentrations of OPA or glutaraldehyde, such as the OPA or glutaraldehyde disinfectants, OPA or glutaraldehyde could be measured directly without making derivatives first. OPA or glutaraldehyde may be analyzed easily with GC analysis. For non-chromatographic analysis, OPA or glutaraldehyde could be measured directly with spectrophotometric methods. However, one drawback to this method is that there must be no interference at the specific wavelength used. For example, OPA or glutaraldehyde could be oxidized slowly by air and the carboxylic acid formed may interfere in such assays.

All three instrumental methods involve the preparation of samples and use of an instrument. They are all time-consuming and too expensive or too complicated for hospital end users. Therefore, Albert Browne and 3M have developed a simple strip procedure for a Pass/Fail test. In such a test, the strip was dipped into either OPA or glutaraldehyde solutions for a certain amount of time. After a predetermined time, the strip color was compared with some standard colors. Their strip chemistry principles were not released. The problems with this method are consistency and accuracy. The strip method has the following problems (1). Good solutions (OPA or glutaraldehyde higher than "POI", the point of interest) often fail the test for different reasons. (2). The soaking time and waiting time have to be controlled carefully. Any deviation will lead to different shades of color and a false reading. (3). Moving of the strip when soaking will lead to the loss of chemical reagents to the OPA or glutaraldehyde solutions leading to false reading. (4). Individual users have different color recognition habits and often have a different opinion of the end-color. (5). The final color is dependent on many factors and is particularly sensitive to time.

The current invention provides another method without the above problems. Although the chemistry principle could also be used for the strip approach, in a preferred embodiment it is used for the color change of a solution.

SUMMARY OF THE INVENTION

The present invention pertains to a liquid measuring device that measures a fixed volume of liquid including a first barrel having a proximal and distal end and a gas or vapor permeable but liquid impermeable barrier situated in the barrel between the proximal and distal ends, whereby the liquid can only be filled up to the barrier. In a preferred embodiment, the volume in the barrel up to the barrier equals the fixed volume. The liquid measuring may further include a means to position the barrier to deliver a fixed volume of liquid, whereby the liquid can only be filled up to the barrier.

In a preferred embodiment, the liquid measuring device further includes a coupling device to adapt the barrier to the measuring device. In a more preferred embodiment, the coupling device includes an insert. In a most preferred embodiment, the insert is movable in the barrel. In another most preferred embodiment, the liquid measuring device further includes a holder to position and secure the insert in the liquid measuring device. In an alternate preferred embodiment, the insert is moved to a desired position by means of a screw.

In a preferred embodiment, the liquid measuring device is a pipette or syringe.

In a preferred embodiment, the liquid measuring device further includes a second barrel which is in fluid communication with said first barrel by means of a valve. In a preferred embodiment, the valve is a one-way valve. In an alternate preferred embodiment, the valve has an on/off switch.

In a preferred embodiment, the liquid measuring device may further include a needle at the distal end.

In a preferred embodiment, the insert of the liquid measuring device is H-shaped in cross-sectional view. In an alternate preferred embodiment, the insert is U-shaped in cross-sectional view.

In a preferred embodiment, the first barrel of the liquid measuring device includes a valve at the distal end. In a more preferred embodiment, the valve is a one-way valve. In an alternate more preferred embodiment, the valve is an on/off valve. In a preferred embodiment, the gas or vapor permeable but liquid impermeable barrier of the liquid measuring device comprises hydrophobic material.

The present disclosure also pertains to a method of measuring a fixed volume of liquid including the steps of:

1) providing a gas or vapor permeable but liquid impermeable barrier in a barrel having a proximal end and a distal end;

2) inserting the distal end into a sample comprising liquid fluid;

3) creating a negative pressure on the proximal end; and 4) transferring the liquid fluid from the sample into the barrel, wherein the liquid fluid can only be filled up to the barrier.

In a preferred embodiment, the method further includes adjusting the position of the barrier in the barrel. In a preferred embodiment, the barrier is part of a coupling device and the method further includes adapting the coupling device to the barrel. In a more preferred embodiment, the adapting includes inserting the coupling device into the barrel.

In a preferred embodiment, the barrel further includes a valve at the distal end and the method further includes opening and/or closing the valve.

In a preferred embodiment, the method further includes pulling a plunger in the barrel to create a negative pressure.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 1 shows the basic principles of the described assay. Reaction 1 shows the reaction of aldehyde with compound X to produce a compound with a first color. Preferably, the first color is colorless. Reaction 2 shows the reaction of aldehyde and Y to form a compound with a second color. Preferably, reaction 2 is slower than Reaction 1. If the concentration of aldehyde is below the POI (point of interest) only compound X will react and the resulting solution will be the first color as shown in the bottom half of the figure. In the presence of a level of aldehyde that is equal to or more than the POI, a solution with the second color or the combined color of the first color and the second color will be formed.

FIGS. 6A and 6B show embodiments of the liquid delivery apparatus with all chemicals in one chamber. FIG. 6C shows a two chambered embodiment of the liquid delivery apparatus. The test sample may be taken into the first chamber for reaction with the first compound such as compound X in FIG. 1. Then the sample is moved by means of a one-way valve or a manual ON/OFF valve 8 into the second chamber where the test sample reacts with the second compound such as compound Y of FIG. 1.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Aldehydes react with amino-containing compounds like amino acids or amines to form an imine or more commonly known as a Schiff's base, which is often colored. Taking glycine as an example:

(Green to Black, changing from lighter to darker)

Schiff's Base Formation Between OPA and Glycine

Another known aldehyde reaction is the sodium bisulfite carbonyl addition reaction.

(Colorless)

Addition Reaction of Sodium Bisulfite to OPA

The sodium bisulfite addition reaction is more favorable than that of Schiff's formation since the former reaction is fast and hard to reverse. Thus, in the presence of both a compound containing an amino group such as an amino acid and a reagent such as sodium bisulfite, the aldehyde will react first with sodium bisulfite and then with the amino acid. Therefore, it is possible to design a color pass/fail reaction by controlling the amount of reagents to react with aldehydes such as formaldehyde, OPA or glutaraldehyde. The key is the amount of reagent such as sodium bisulfite which is designed to react with the aldehyde without a color being developed in the presence of an amino acid. Any remaining aldehyde will then react with the amino acid to develop a colored solution. This confirms the presence of a certain amount of an aldehyde such as formaldehyde, OPA or glutaraldehyde in a test solution such as a disinfectant solution. On the other hand, if no color was developed, it confirms that the formaldehyde, OPA or glutaraldehyde concentration is below an acceptable specification. The specific concentration can be set to any point by adjusting the amounts of the chemical reagents used or by using different amounts of aldehyde (formaldehyde, OPA or glutaraldehyde) in the test solution.

Thus, a color pass/fail reaction for determination of excess aldehyde by control of reagents which react with aldehyde is described. The key is the amount of reagent such as sodium bisulfite which is designed to react with the Point of Interest (POI) level of aldehyde without a color being developed in the presence of a compound containing an amino group such as an amino acid. Any "extra" aldehyde, exceeding the POI, will then react with the compound containing an amino group, causing a color to be developed. In a preferred embodiment, the aldehyde is either OPA or glutaraldehyde and the compound containing the amino group is an amino acid. This method is especially useful for quality control where components only needed to be examined in pre-determined ranges.

A number of reagents which are known to react quickly with aldehydes may be used in the practice of the invention. These include any chemicals which can oxidize or reduce the aldehyde group and any chemicals which can react with and alter the carbonyl functional group of the aldehyde. Examples of such reagents are disclosed in Morrison & Boyd, "Organic Chemistry", Chapter 19, Allyn and Bacon, $3^{rd}$ edition, 1973, which is herein incorporated by reference. Such reagents include, but are not limited to, $Ag(NH_3)_2$; $KMnO_4$; $K_2Cr_2O_7$; $H_2$+Ni, Pt, or Pd; $LiAlH_4$ or $NaBH_4$, then $H^+$; Zn (Hg), conc. HCl; $NH_2NH_2$, base; Grignard reagents; salts of cyanide and bisulfite; ammonia derivatives such as hydroxylamine, hydrazine, phenylhydrazine, and semicarbazide; reactions with alcohols in the presence of acid; and reactions with acid or base such as the Cannizzaro reaction, the aldol condensation, and the Perkin condensation. In a preferred embodiment, the reagent which reacts with the aldehyde is a salt of either bisulfite or cyanide.

Figure 1:
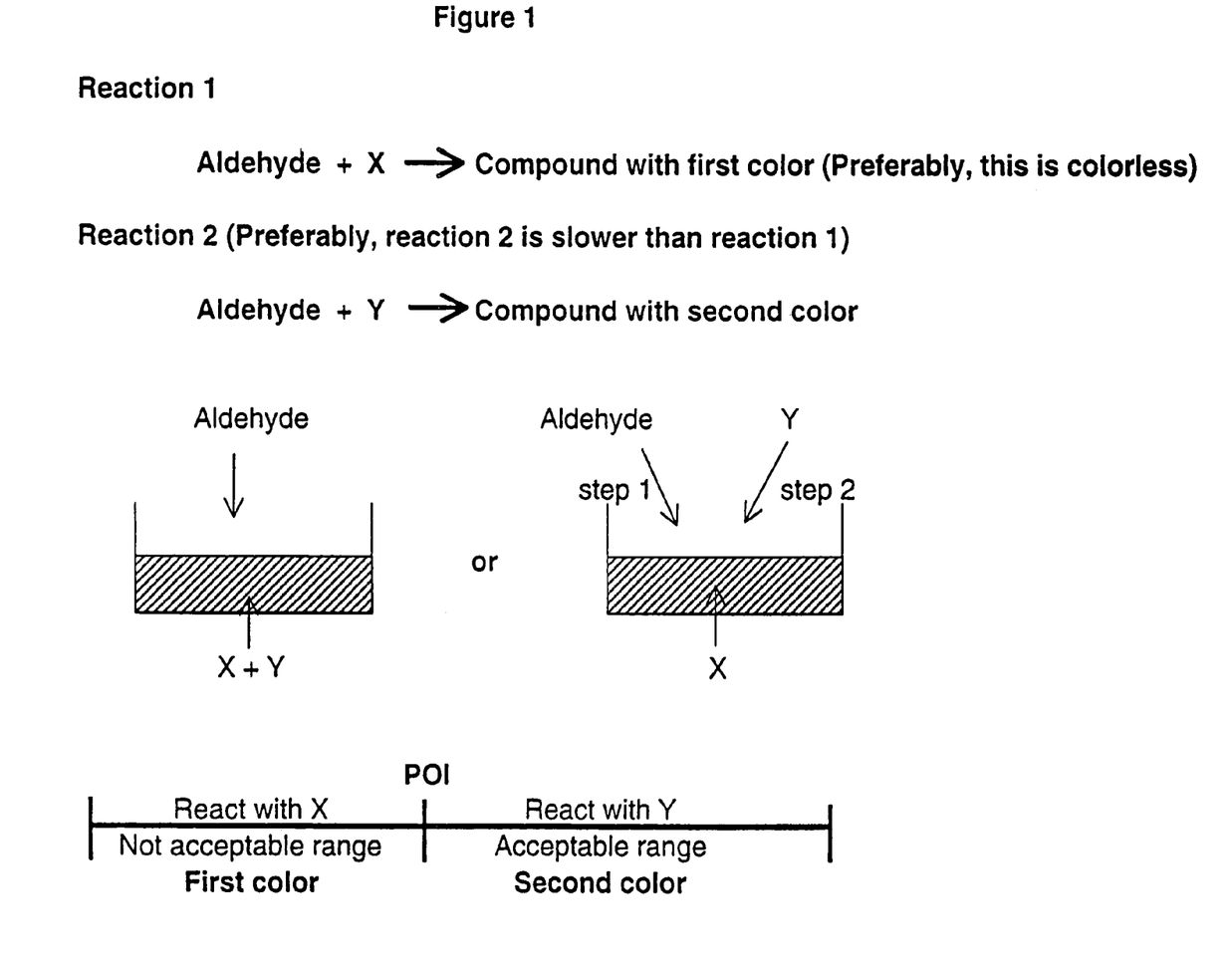

This aspect of the invention is illustrated in FIG. 1. Both compounds X and Y react with the aldehyde in the figure. Preferably X reacts much faster than Y. Preferably, the reaction of X with aldehyde results in a colorless compound whereas the reaction of Y with aldehyde results in a colored compound. A point of interest is chosen and the amount of X that will react with the point of interest is determined. When the aldehyde is mixed with X and Y, the aldehyde will react first with compound X which is kinetically and thermodynamically favored. Any excess aldehyde will then react with compound Y to form a colored solution. Consequently, if a colored solution results, the concentration of aldehyde is above the point of interest. The determination may be made visually, with or without a color chart. Alternatively, a spectrophotometer may be used. If the reaction between the aldehyde and compound X is not kinetically and thermodynamically favored, then compound Y can be added after the aldehyde reacts with compound X as shown in FIG. 1.

The theoretical amount of OPA: sodium bisulfite is 1:2. However, it was found that less sodium bisulfite is needed to react with OPA than the theoretical amount in order to get a good color display.

Another aspect of the invention is a liquid-measuring device, such as a pipette or syringe, for carrying out the assay. This device could be used for any "fixed-volume" measurement and transfer in chemistry, biochemistry, clinical chemistry or other industries.

The apparatus may be a syringe or pipette with one or more barrels and plungers and a membrane barrier with or without a coupling device. The membrane barrier is a gas or vapor permeable and liquid impermeable barrier. In the presence of certain pressure differences between the two sides of the barrier, the gas or vapor flows through the membrane but not the liquid. Any suitable gas or vapor permeable and liquid impermeable materials can be used for this purpose. Some examples include, but are not limited to, nonwoven polyolefin, such as Tyvek™ (non-woven polyethylene), or CSR (non-woven polypropylene central supply room), wrapping material and any other hydrophobic filtering materials. Optionally, the device contains an insert and a holder. The syringe or pipette apparatus may also contain valves to control the flow of liquid.

The membrane barrier can be thermally bound to the syringe or pipet. It can also be attached to the syringe or pipet with an adhesive or connected to the syringe barrel by a coupling device. The coupling device may be connected to an insert for altering the position of the membrane barrier. The position of the membrane barrier can be adjusted by the length of the insert. The insert may be secured with a holder.

The membrane barrier is a gas or vapor permeable but liquid impermeable barrier. The membrane barrier is positioned such that the liquid can only be filled up to the barrier. The invention has several preferred embodiments.

Figure 2:
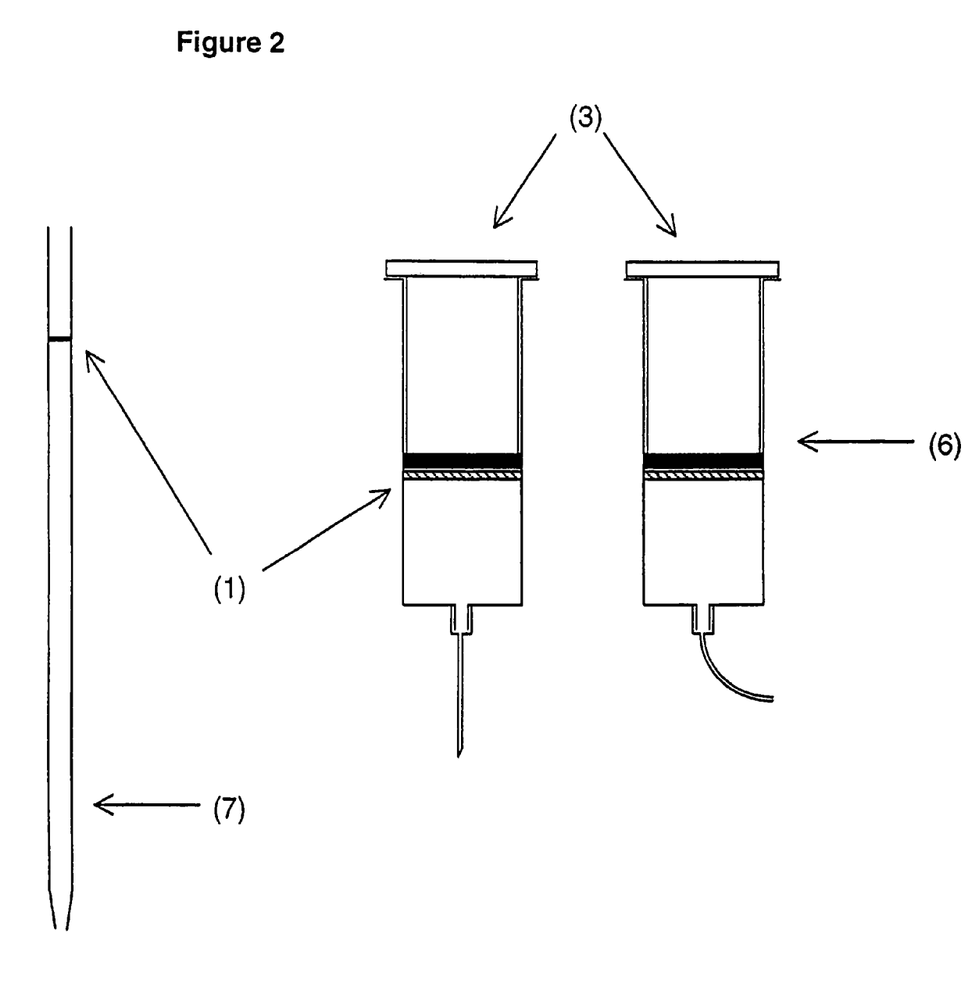
FIG. 2 shows a pipette and two variants of a syringe with a gas or vapor permeable liquid impermeable barrier.

In the first embodiment (FIG. 2), a gas or vapor permeable liquid impermeable membrane 1 is fixed into the pipette 7 or syringe 6 and held in place at the desired maximum volume by means known in the art. The syringe includes a plunger 3. The syringe can have a metal or plastic needle with or without a needle cap. In one embodiment (FIGS. 3A-3D), a coupling device 2 is used which is larger or smaller than the diameter of the pipette 7 or syringe 6. Two parts of the pipet or syringe with different lengths can be joined together with such a coupling device.

Figures 3, 3C:
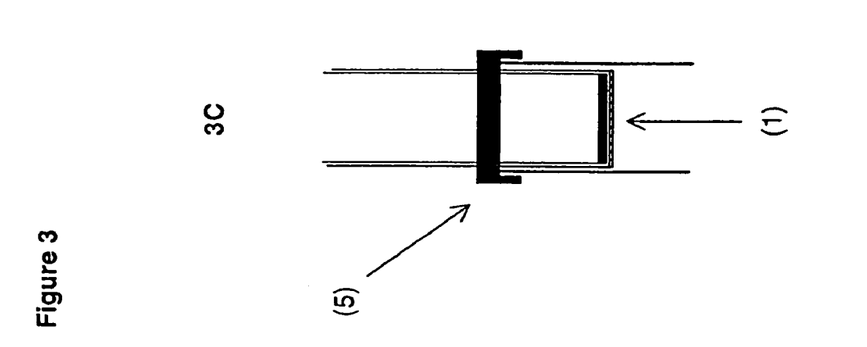
FIG. 3C illustrates a holder 5 that holds the inserts in place.
Figure 3A:
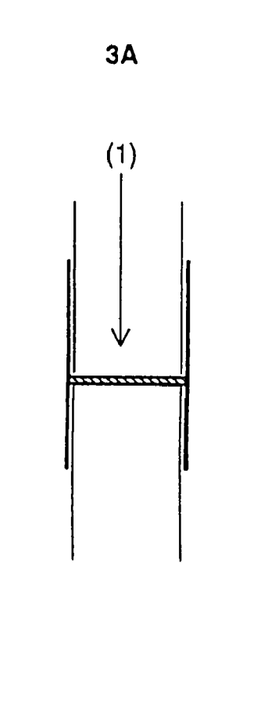
FIG. 3A shows the coupling of the gas or vapor permeable liquid impermeable barrier to the syringe or pipette.
Figure 3B:
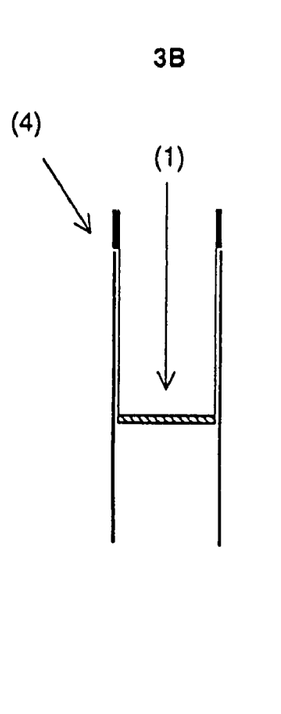
FIG. 3B illustrates how inserts 4 at the top of the pipette or syringe attach the gas or vapor permeable liquid impermeable barrier to the pipette or syringe.
Figure 3D:
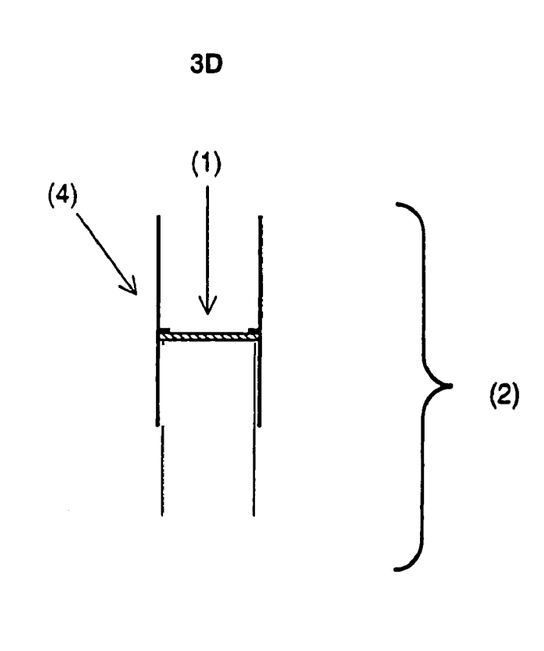
FIG. 3D shows the inserts and the coupling of the gas or vapor permeable liquid impermeable barrier.
Figure 4:
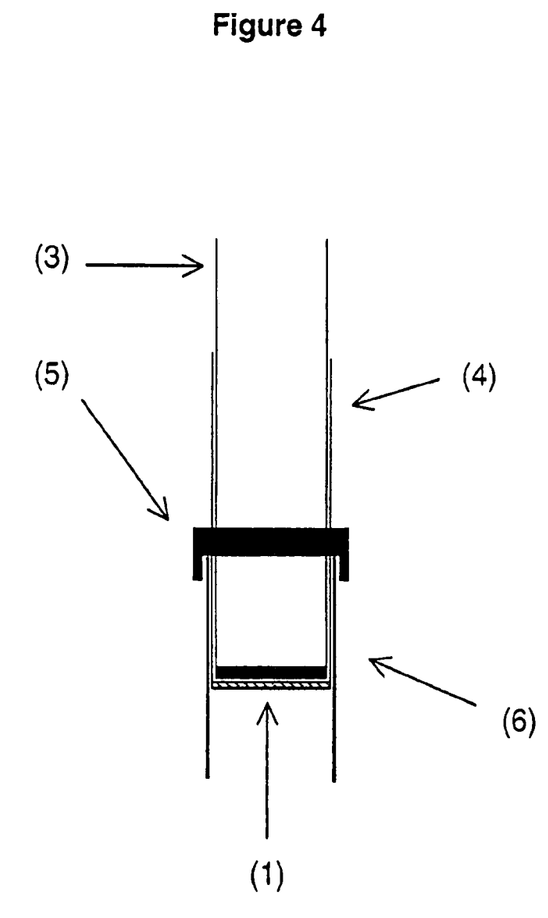
FIG. 4 is an expanded view of FIG. 3C which shows a gas or vapor permeable liquid impermeable barrier 1, an insert 4, and a holder 5.
Figure 5:
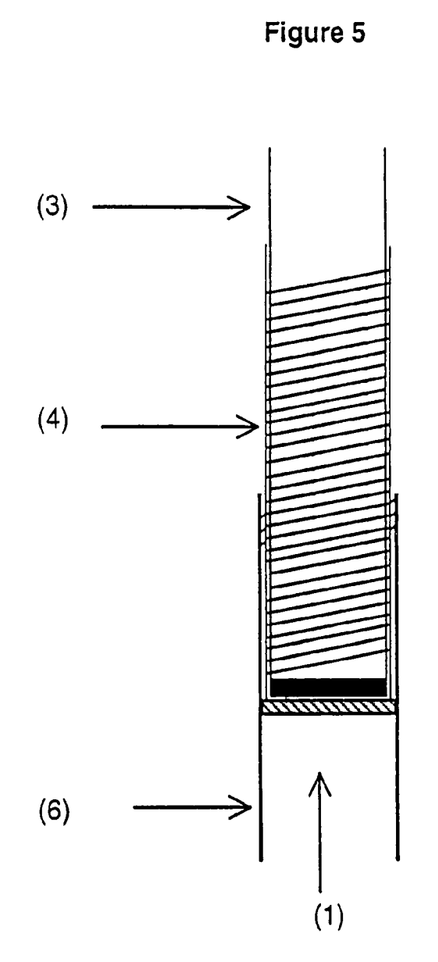
FIG. 5 shows one embodiment of the invention where the position of the gas or vapor permeable liquid impermeable membrane is adjusted by means of a screw.

Coupling of the membrane barrier to the syringe or pipette is shown in FIGS. 3A, 3B, 3C, 3D and FIG. 4. The membrane can be inserted into the syringe or pipet from the top of the pipette or syringe by an insert 4 which may be secured with a holder 5 and its position varied by any means known in the art such as by a screw (FIG. 5) or a slidable adjustment (FIG. 4). FIG. 3D shows an insert which has a larger diameter than the pipette or syringe. By adjusting the insert and creating a negative pressure on the upper part of the pipette or syringe, the fluid can be loaded into the syringe or pipette up to the barrier.

Figure 6:
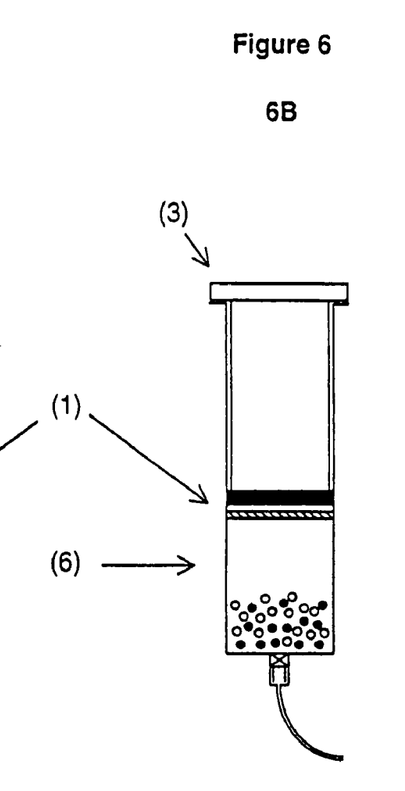

FIGS. 6A, 6B and 6C illustrate the use of the measuring device with this invention. FIGS. 6A and 6B show a syringe with a gas or vapor permeable liquid impermeable barrier and two chemicals. The liquid can be filled in the syringe by inserting the plastic needle into the sample solution, pulling the plunger to create a negative pressure in the syringe, and loading the liquid into the syringe. The measuring device can have a filtering material (FIG. 6A) or valve (FIG. 6B) to retain the chemicals in the barrel. The chemical in the syringe can be in either a liquid or solid form. The valve can be a one-way valve or a manual ON/OFF valve.

FIG. 6C provides another embodiment for mixing more than one reactant successively. It has two chambers 9, 10. A fixed volume of any solution including, but not limited to an aldehyde is drawn up through a one-way valve or an ON/OFF valve 8 into the first chamber 9 where it mixes with the first reactant, for example sodium bisulfite. After a predetermined time, the reactants flow through a second one-way valve or an ON/OFF valve 8 into a second reaction chamber 10 which might contain an amine such as lysine, for example, to complete the reaction. Alternatively, a three-way valve can be used instead of two one-way valves.

The invention has several advantages over the prior art methods. First, the pass/fail conclusion is consistent and convenient. Preferably, there is no need to guess the color. The user's only conclusion will be "colored" or "not colored." Second, the liquid transferring device is consistent and convenient. A fixed volume of liquid can be taken by a simple operation. Third, the solution color is easier to visualize than a test strip paper since the test strip paper itself is colored, leading to false positive results. Fourth, the color displaying time can be adjusted by adding a base to make the reaction faster or an acid to make the reaction slower. Fifth, the color being displayed can be adjusted by choosing different amino acids or amines. Sixth, the darkness of the color being displayed can be adjusted by the amount of the amino acids or amines. Seventh, the assay is extremely easy to run and interpret. And finally, the liquid transferring device could be used for any "fixed-volume" transfer in chemistry, biochemistry, clinical chemistry or other industries.

EXAMPLES

Example 1

Effect of OPA to Sodium Bisulfite Mole Ratio (0.5:1 to 8:1)

Sodium bisulfite, glycine and OPA were added in sequence. The OPA to sodium bisulfite mole ratio was ;1 adjusted from 0.5:1 to 8:1 (Table 1). Table 1 shows that the solution with a 2:1 ratio developed a color while a 1:1 ratio did not show color in one week.

It was found that less than the theoretical amount of sodium bisulfite was needed to react with the OPA. This indicates the OPA solutions in this concentration region can be differentiated by observing the color of the solution after a specified time (as in Vial 2 and Vial 3). Since we can control the volume of OPA in testing, we can theoretically test an OPA solution in any concentration range.

TABLE 2

|  | Vial 1 | Vial 2 | Vial 3 | Vial 4 | Vial 5 |
| --- | --- | --- | --- | --- | --- |
| $NaHSO_3$ (82 mM) | 200 µl (0.0164 mMole) | 200 µl (0.0164 mMole) | 200 µl (0.0164 mMole) | 200 µl (0.0164 mMole) | 200 µl (0.0164 mMole) |
| Glycine (82 mM) | 1600 µL (0.1312 mMole) | 1600 µL (0.1312 mMole) | 1600 µL (0.1312 mMole) | 1600 µL (0.1312 mMole) | 1600 µL (0.1312 mMole) |
| OPA (0.55%, 41 mM) | 400 µL (0.00164 mMole | 500 µL (0.0205 mMole) | 600 µL (0.0246 mMole) | 700 µL (0.0278 mMole) | 800 µL (0.0328 mMole) |
| OPA:$NaHSO_3$ mole ratio | 1:1 | 1.25:1 | 1.5:1 | 1.75:1 | 2:1 |
| Time to develop color | Never | Never | Never | 13' | 5' |
| Initial color | Colorless | Colorless | Colorless | Very light Pink | (Light) Yel/Grn |
| Final color (after 30') | Colorless | Colorless | Colorless | Green | Dark Grn |

In Table 2, the reaction volume is varied by varying the amount of OPA solution from 400 µl to 800 µl. The assay is independent of volume. The OPA to sodium bisulfite mole ratio is a key parameter of the assay.

Example 3

OPA Concentration Variation Study in the OPA to Sodium Bisulfite Mole Ratio 1:1 to 2:1 Region. (Same Volume Different Concentration)

Sodium bisulfite, glycine and OPA were added and the OPA to sodium bisulfite mole ratio was adjusted as in Example 2. As shown in Table 3, the first POI was in the range of 6'20"-7'20" range and the time needed for color change was very consistent. However, for the second POI, there was some variation for this time (17-24'). Without being bound by any mechanism, this may be due to the visual limitation or it may mean that at diluted concentration, the color development is more likely to be influenced by micro reaction condition variations, such as temperature, pH or even the exposure of sunlight.

TABLE 3

|  | Vial 1 | Vial 2 | Vial 3 | Vial 4 | Vial 5 |
|---|---|---|---|---|---|
| NaHSO₃ (82 mM) | 200 μl (0.0164 mMole) | 200 μl (0.0164 mMole) | 200 μl (0.0164 mMole) | 200 μl (0.0164 mMole) | 200 μl (0.0164 mMole) |
| Glycine (82 mM) | 1600 μL (0.1312 mMole) | 1600 μL (0.1312 mMole) | 1600 μL (0.1312 mMole) | 1600 μL (0.1312 mMole) | 1600 μL (0.1312 mMole) |
| OPA (%) | 0.275 (20.50 mM) | 0.344 (25.63 mM) | 0.413 (30.75 mM) | 0.481 (35.88 mM) | 0.550 (41.00 mM) |
| ml (0.55% OPA) to dilute to 100 ml with water | 50.00 | 62.50 | 75.00 | 87.50 | No dilution |
| OPA solution used | 800 μl | 800 μl | 800 μl | 800 μl | 800 μl |
| OPA mMole | 0.0164 | 0.0205 | 0.0246 | 0.0287 | 0.0328 |
| OPA:NaHSO₃ mole ratio | 1:1 | 1.25:1 | 1.5:1 | 1.75:1 | 2:1 |
| Time to develop color | Never | Never | Never | 17-20' | 6'20"-7'20" |
| Time to develop color, repeat #1 | Never | Never | Never | 18-21' | 6'20"-7'20" |
| Time to develop color, repeat #2 | Never | Never | Never | 19-21' | 6'20"-7'20" |
| Time to develop color, repeat #3 | Never | Never | Never | 21-23' | 6'20"-7'20" |
| Time to develop color, repeat #4 | Never | Never | Never | 22-24' | 6'20"-7'20" |
| Initial color | Colorless | Colorless | Colorless | Very light pink | (Light) Yel/Grn |
| Final color (after 2 h) | Colorless | Colorless | Colorless | Dark Grn | Dark Grn |

Example 4

OPA Concentration Variation Study

Sodium bisulfite, glycine and OPA were added as in Example 1. Since the POI position is controlled by the OPA to sodium bisulfite mole ratio, by changing the OPA volume, one should be able to switch the POI to basically any OPA concentration range. Thus, in Table 4, the actual OPA moles taken in Vial 1, Vial 2 and Vial 3 are equal to Vial 3, Vial 4 and Vial 5 in Table 3.

TABLE 4

|  | Vial 1 | Vial 2 | Vial 3 |
|---|---|---|---|
| NaHSO₃ (82 mM) | 200 μl (0.0164 mMole) | 200 μl (0.0164 mMole) | 200 μl (0.0164 mMole) |
| Glycine (82 mM) | 1600 μL (0.1312 mMole) | 1600 μL (0.1312 mMole) | 1600 μL (0.1312 mMole) |
| OPA (%, 41 mM) | 0.275 | 0.344 | 0.413 |
| ml (0.55% OPA) to dilute to 100 ml | 50.00 | 62.50 | 75.00 |
| OPA solution used | 1201 μl (0.0246 mMole) | 1119 μl (0.0287 mMole) | 1065 μl (0.0328 mMole) |
| OPA:NaHSO₃ mole ratio | 1.5:1 | 1.75:1 | 2:1 |
| Time to develop color (up to 30') | Never | 16' | 5' |
| Initial color | Colorless | (light) Yel/Grn | (Light) Yel/Grn |

Thus, one of the key factors for this invention is the mole ratio of aldehyde to sodium bisulfite. Similar results were obtained for DL-alanine, c-amino-n-caproic acid and L-lysine, except that different end colors were observed.

Example 5

Further Experiments with OPA for POI's in the Range of 0.35% and 0.30%

Changes due to the type of amino acid and the mole ratio were illustrated in the following example where DL-dopa is used as the amino acid (also see Example 7). Sodium bisulfite, and OPA were added as in Example 1. DL-dopa was substituted for glycine as the amino acid.

TABLE 5

| 82 mM NaHSO3 | Saturated DL-dopa | 0.35% OPA (23.09 mM) | 0.30% OPA (22.37 mM) | 0.35% OPA (23.09 mM) Color in (minutes and seconds) | 0.30% OPA (22.37 mM) Color in (minutes and seconds) |
|---|---|---|---|---|---|
| 100 μl (0.0082 mMole) | 100 μl | 450 μl (0.0119 mMole) | 450 μl (0.0101 mMole) | 2'20"–2'30" | 3'20"–4' |
| 100 μl (0.0082 mMole) | 100 μl | 400 μl (0.0106 mMole) | 400 μl (0.0089 mMole) | 3'00"–3'30" | 5'–10' |
| 100 μl (0.0082 mMole) | 100 μl | 390 μl (0.0103 mMole) | 390 μl (0.0087 mMole) | 3'40"–4'10" | 5'30"–11' |

In the above example, the use of DL-dopa as the amine resulted in an orange color. The type of amino acid, mole ratio, and reaction time are all important to determine the formation of color.

Example 6

Base Effect for the Color Development Time

This example shows that added base promotes the reaction rate so that the color displaying time can be shortened. Thus, a certain amount of base could be added to display the color within a desired period of time.

TABLE 6

|  | Vial 1 | Vial 2 | Vial 3 | Vial 4 |
|---|---|---|---|---|
| NaHSO$_3$ (82 mM) | 200 μl (0.0164 mMole) | 200 μl (0.0164 mMole) | 200 μl (0.0164 mMole) | 200 μl (0.0164 mMole) |
| Glycine (82 mM) | 1600 μL (0.1312 mMole) | 1600 μL (0.1312 mMole) | 1600 μL (0.1312 mMole) | 1600 μL (0.1312 mMole) |
| OPA (%) (variation conc.) | 0.275 | 0.344 | 0.413 | 0.481 |
| ml (0.55% OPA), added to dilute to 100 ml | 50.00 | 62.50 | 75.00 | 87.50 |
| OPA (0.55%, 41 mM)(initial conc.) | 800 μl (0.0164 mMole) | 800 μl (0.0205 mMole) | 800 μl (0.0246 mMole) | 800 μl (0.0287 mMole) |
| OPA:NaHSO$_3$ mole ratio | 1:1 | 1.25:1 | 1.5:1 | 1.75:1 |
| Time to develop color (without NaOH) | colorless | colorless | colorless | Very light pink (17'–24') |
| Time to develop color (100 μL NaOH added) | 1.5 h slight yellow | 1 h slight yellow | 2' yellow | <2', yellow |
| Time to develop color (200 μL NaOH added) | All turned yellow in less than 1'. Too fast. Too much base. | | | |

Note:
Sodium hydroxide was added before OPA.

Conversely, it was found that added acid, such as citric acid, would delay the color display. This would be useful in the case if the color is displayed too soon (data not shown).

Example 7

Other Amino Acids with Added Base (100 μL)

It was found with other amino acids that the displayed colors were different. For example, when reacting with OPA, DL-alanine was bright yellow and for E-amino-n-caproic acid, the color was pink. Furthermore, the reaction rates were also different. Thus both DL-alanine and c-amino-n-caproic acid displayed color significantly later than glycine (data not shown).

Example 8

Activated Cidex Solution (Containing 2.1% Glutaraldehyde) with Lysine To five scintillation vials, glutaraldehyde, sodium bisulfite and lysine were added and mixed. A yellow color developed gradually from Vial 5. No color was observed in Vial 1. The "between" colors were seen from Vial 2 to Vial 4 but they are so "gradual" that they could not be distinguished visually.

TABLE 7

|  | Vial 1 | Vial 2 | Vial 3 | Vial 4 | Vial 5 |
| --- | --- | --- | --- | --- | --- |
| NaHSO₃ (82 mM) | 200 µl (0.0164 mMole) | 200 µl (0.0164 mMole) | 200 µl (0.0164 mMole) | 200 µl (0.0164 mMole) | 200 µl (0.0164 mMole) |
| Lysine (82 mM) | 1600 µL (0.1312 mMole) | 1600 µL (0.1312 mMole) | 1600 µL (0.1312 mMole) | 1600 µL (0.1312 mMole) | 1600 µL (0.1312 mMole) |
| Glutaraldeyde (220 mM) solution used | 74.5 µl (0.0614 mMole) | 93.2 µl (0.0205 mMole) | 111.8 µl (0.0246 mMole) | 130.5 µl (0.0287 mMole) | 149.1 µl (0.0328 mMole) |
| Glutaraldehyde:NaHSO₃ mole ratio | 1:1 | 1.25:1 | 1.5:1 | 1.75:1 | 2:1 |
| Color at 15 minutes | Colorless | Very light yellow to yellow, very gradual. No clear-cut difference | | | Yellow |

This can be explained in light of the stabilities of the compounds involved. First, if aldehyde-sodium bisulfite complex 5 is more stable than aldehyde-sodium bisulfite complex 6, we would see a larger POI range from glutaraldehyde.

(Colorless)

More Stable

5

(Colorless)

Less Stable

6

The Ranges of POI Are Related to the Stability of Compound 5 and 6.

Or in more accurate terms, the different POI ranges from OPA and glutaraldehyde might be a result of the competence of aldehyde-sodium bisulfite formation and the aldehyde/amino acid Schiff's base formation both kinetically and thermodynamically.

be applied generally to aldehydes and amines to provide a pass/fail type assay of aldehyde content.

Example 10

The above chemistry principle may be applied in the reaction of aldehydes and compounds containing an amino group generally. This example shows the reaction of glutaraldehyde and sodium cyanide using either glycine or lysine as the amino acid. The formation of corresponding two aldehyde cyanide addition compounds are shown as below.

1

(OPA)

10

(Colorless)

TABLE 8

|  | Vial 1 | Vial 2 | Vial 3 | Vial 4 | Vial 5 |
| --- | --- | --- | --- | --- | --- |
| NaHSO₃ (82 mM) | 200 µl (0.0164 mMole) | 200 µl (0.0164 mMole) | 200 µl (0.0164 mMole) | 200 µl (0.0164 mMole) | 200 µl (0.0164 mMole) |
| Lysine (82 mM) | 1600 µL (0.1312 mMole) | 1600 µL (0.1312 mMole) | 1600 µL (0.1312 mMole) | 1600 µL (0.1312 mMole) | 1600 µL (0.1312 mMole) |
| Glutaraldehyde (220 mM) solution used | 74.5 µl (0.0614 mMole) | 93.2 µl (0.0205 mMole) | 111.8 µl (0.0246 mMole) | 130.5 µl (0.0287 mMole) | 149.1 µl (0.0328 mMole) |
| Glutaraldehyde:NaHSO₃ mole ratio | 1:1 | 1.25:1 | 1.5:1 | 1.75:1 | 2:1 |
| Color at 15' | Colorless | light yellow | yellow | yellow | yellow |

A narrower POI range was observed for glutaraldehyde reacting with lysine and sodium bicarbonate. Adding the amino acid (lysine) last was the key. Table 8, shows a clear color difference between Vial 1 (color less) and Vial 3 (yellow). Thus by allowing the glutaraldehyde and sodium bisulfite to react first and then adding lysine, results are similar to those observed with OPA above.

Depending on the chemicals used, the time may vary. For NaHSO₃, the lysine can be added immediately after the aldehyde is mixed with the NaHSO₃. Thus the assay described can 8
(Glutaraldehyde)

11
(Colorless)

The Formation of Colorless Aldehyde-Cyanide Addition Compounds 10 and 11

To each of the 5 scintillation vials, glutaraldehyde and sodium cyanide were added and mixed first (Table 9), and lysine solution was added last. A yellow color developed from Vial 5 but not from the other vials. A POI was identified between Vial 4 and Vial 5.

The aldehyde solution can be measured and transferred by means known in the art such as by a regular pipet or syringe. In a preferred embodiment, the aldehyde solution can be measured and transferred using a liquid measuring device as described herein which features a gas or vapor permeable, liquid impermeable, membrane. The use of the liquid measuring device containing the gas or vapor permeable, liquid impermeable membrane of the present disclosure has the advantage that the liquid can be transferred easily using a simple operation with consistent results.

Compound X and Compound Y (FIG. 1) may be in one vial or in two separate vials. They may be transferred using either a pipet or syringe. The aldehyde may be added to compound X and the resulting mixture added to compound Y, the aldehyde may be added to compounds X and Y together, or the aldehyde and chemical Y can be added to the chemical X consecutively. The measuring and/or transferring of the aldehyde test sample can be conducted with a regular pipet or syringe. The gas or vapor permeable liquid impermeable barrier adds many benefits as described previously.

TABLE 9

Glutaraldehyde:Sodium Cyanide Mole Ratio (0.125:1 to 2:1).

|  | Vial 1 | Vial 2 | Vial 3 | Vial 4 | Vial 5 |
| --- | --- | --- | --- | --- | --- |
| NaCN (82 mM) | 200 µl (0.0164 mMole) | 200 µl (0.0164 mMole) | 200 µl (0.0164 mMole) | 200 µl (0.0164 mMole) | 200 µl (0.0164 mMole) |
| Glycine (82 mM) | 1600 µL (0.1312 mMole) | 1600 µL (0.1312 mMole) | 1600 µL (0.1312 mMole) | 1600 µL (0.1312 mMole) | 1600 µL (0.1312 mMole) |
| Glutaraldehyde (220 mM) solution | 9.3 µl (0.0020 mMole) | 18.6 µl (0.0041 mMole) | 37.3 µl (0.0082 mMole) | 74.5 µl (0.0164 mMole) | 149.1 µl (0.0328 mMole) |
| Glutaraldehyde:NaCN mole ratio | 0.125:1 | 0.25:1 | 0.5:1 | 1:1 | 2:1 |
| Final color in 7' | Colorless | Colorless | Colorless | Colorless | Yellow |

Example 11

To each of the 5 scintillation vials, glutaraldehyde and sodium cyanide were added and mixed first, and lysine solution was added last (Table 10). A yellow color developed from Vial 2 to Vial 5 but not recognizable from Vial 1. A PO was identified between Vial 1 and Vial 3. It is only practical with the naked eye to differentiate the colors between Vial 1 and Vial 3. That is, it would be challenging to distinguish the difference between Vial 1 and Vial 2 or between Vial 2 and Vial 3. Thus we may conclude that no narrower POI could be identified unless an instrument is employed.

In one embodiment, shown in FIG. 6C, the Compound X may be in a first chamber 9. The aldehyde is drawn up through the valve 8 up to the gas or vapor permeable, liquid impermeable barrier 1. After a predetermined time, the aldehyde and compound X are transferred to a second chamber 10 through a valve 8 which is either a one-way or an on/off valve, where they react with compound Y. After a pre-determined time, the color in the second chamber is observed and the presence or absence of excess aldehyde in the test sample is determined.

It will be understood by those of skill in the art that numerous and various modifications can be made without departing

TABLE 10

Glutaraldehyde:Sodium Cyanide Mole Ratio (1:1 to 2:1).

|  | Vial 1 | Vial 2 | Vial 3 | Vial 4 | Vial 5 |
| --- | --- | --- | --- | --- | --- |
| NaCN (82 mM) | 200 µl (0.0164 mMole) | 200 µl (0.0164 mMole) | 200 µl (0.0164 mMole) | 200 µl (0.0164 mMole) | 200 µl (0.0164 mMole) |
| Glycine (82 mM) | 1600 µL (0.1312 mMole) | 1600 µL (0.1312 mMole) | 1600 µL (0.1312 mMole) | 1600 µL (0.1312 mMole) | 1600 µL (0.1312 mMole) |
| Glutaraldehyde (220 mM) solution used | 74.5 µl (0.0164 mMole) | 93.2 µl (0.0205 mMole) | 111.8 µl (0.0082 mMole) | 130.5 µl (0.0164 mMole) | 149.1 µl (0.0328 mMole) |
| Glutaraldehyde:NaCN mole ratio | 1:1 | 1.25:1 | 1.5:1 | 1.75:1 | 2:1 |
| Time to develop color | Never | 3' | 2' | 1' | 1' |
| Color in ~8 minutes | Colorless | Very light Yellow | Yellow | Yellow | Yellow |

What is claimed is:

1. A liquid measuring device that measures a fixed volume of liquid comprising:
   a first barrel having a proximal and distal end;
   a coupling device comprising a gas or vapor permeable but liquid impermeable barrier on a second barrel, said second barrel being movable along said first barrel to adapt said barrier to the measuring device, whereby the fixed volume of liquid is adjusted by moving said coupling device along said first barrel by means of a screw;
   a gas, vapor and liquid impermeable element adapted to the measuring device to provide a pressure difference between two sides of said barrier such that the liquid can only be filled from said distal end of said first barrel up to said barrier; and
   a valve at said distal end.

2. The liquid measuring device of claim 1, wherein the volume in said first barrel up to said barrier equals the fixed volume.

3. The liquid measuring device of claim 1, further comprising a holder to position and secure said coupling device in the liquid measuring device.

4. The liquid measuring device of claim 1, which is a syringe.

5. The liquid measuring device of claim 1, which further comprises a third barrel which is in fluid communication with said first barrel by means of a valve.

6. The liquid measuring device of claim 1, wherein said gas or vapor permeable but liquid impermeable barrier comprises hydrophobic material.

7. A method of measuring a fixed volume of liquid comprising:
   (a) providing a device comprising:
      (i) a first barrel having a proximal and distal end;
      (ii) a coupling device comprising a gas or vapor permeable but liquid impermeable barrier which is movable along the first barrel to adapt the barrier to the measuring device, whereby the fixed volume of liquid is adjusted by moving the coupling device along the first barrel by means of a screw; and
      (iii) a gas, vapor, and liquid impermeable element adapted to the measuring device to provide a pressure difference between two sides of the barrier such that the liquid can only be filled from the distal end of the first barrel up to the barrier;
   (b) moving the gas or vapor permeable but liquid impermeable barrier along the first barrel to adjust the fixed volume;
   (c) filling a volume formed by the distal end of the first barrel to the barrier with liquid wherein the volume is equal to the fixed volume; and
   (d) closing a valve after filling the device.

8. The method of claim 7, wherein the coupling device comprises a second barrel and the barrier is on the second barrel.

9. The method of claim 8, wherein moving the gas or vapor permeable but liquid impermeable barrier along the first barrel is by changing the relative position of the first barrel to the second barrel.

10. The method of claim 7, further comprising securing the coupling device to the first barrel.

11. A liquid measuring device configured to measure a fixed volume of liquid, the measuring device comprising:
   a barrel;
   a gas or vapor permeable but liquid impermeable barrier, wherein said barrier is movable relative to said barrel;
   a screw adjustment member configured to move said barrier relative to said barrel; and
   a plunger configured to be moved relative to said barrel to draw the fixed volume of liquid into said barrel up to said barrier.

* * * * *